(12) United States Patent
Merlo

(10) Patent No.: US 9,498,269 B2
(45) Date of Patent: Nov. 22, 2016

(54) PERCUSSION DEVICE FOR BONE IMPLANTOLOGY AND OPERATING METHOD THEREOF

(76) Inventor: Mario Merlo, Milan (IT)

(\*) Notice: Subject to any disclaimer, the term of this patent is extended or adjusted under 35 U.S.C. 154(b) by 598 days.

(21) Appl. No.: 14/111,914

(22) PCT Filed: Apr. 13, 2012

(86) PCT No.: PCT/IB2012/051835
§ 371 (c)(1),
(2), (4) Date: Dec. 13, 2013

(87) PCT Pub. No.: WO2012/140615
PCT Pub. Date: Oct. 18, 2012

(65) Prior Publication Data
US 2014/0228855 A1      Aug. 14, 2014

(30) Foreign Application Priority Data

Apr. 14, 2011   (IT) .............................. MI2011A0634

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/84* | (2006.01) | |
| *A61C 1/07* | (2006.01) | |
| *A61C 8/00* | (2006.01) | |

(52) U.S. Cl.
CPC .............. *A61B 17/846* (2013.01); *A61C 1/07* (2013.01); *A61C 8/0089* (2013.01)

(58) Field of Classification Search
CPC combination set(s) only.
See application file for complete search history.

(56) References Cited

U.S. PATENT DOCUMENTS

| | | | |
|---|---|---|---|
| 2,480,451 A | 8/1949 | De La Torre | |
| 6,171,312 B1 * | 1/2001 | Beaty ................. | A61B 17/1604 606/80 |

FOREIGN PATENT DOCUMENTS

GB        316 478 A      8/1929

OTHER PUBLICATIONS

International Search Report, dated Jul. 4, 2012, from corresponding PCT application.

\* cited by examiner

*Primary Examiner* — Sameh Boles
(74) *Attorney, Agent, or Firm* — Young & Thompson

(57) ABSTRACT

A percussion device for bone implantology includes a body housing an electromagnetic coil for the acceleration of a percussion anchor and from which a stem of a metal tool projects, a sonic rod which runs through the core of the electromagnetic coil and along which the percussion anchor is slidable, the sonic rod including a terminal head with which the stem of a metal tool is integrally engageable, a floating yoke arranged in the proximity of the terminal head which acts as travel end stop for the anchor, and wherein the electromagnetic coil is energized impulsewise with an electric current of a duration below 20 milliseconds and energy ranging between 0.8-1.2 KW, to produce an impact of the anchor on the yoke which develops an energy transferred to the tool stem through a sonic wave and a translational momentum, the force developed ranging between 60 and 260 daN.

17 Claims, 7 Drawing Sheets

| M | MASS |
| A1 | SECTION OF STEM S |
| A2 | SECTION OF HOOK |
| P | PROSTHESIS |
| G | HOOK |
| I | IMPULSE |
| S | STEM |
| A2S | SECTION OF STEM |

Key

PERCUSSION DEVICE FOR BONE IMPLANTOLOGY AND OPERATING METHOD THEREOF

FIELD OF THE INVENTION

The present invention refers to a percussion device for bone implantology, in particular for jawbone implantology and orthopedia, and to the operating method thereof.

BACKGROUND ART

In the field of bone surgery, particularly in dental techniques, there is often the need to act on the jawbones and on the lower jawbones, with invasive and traumatic operations.

One of the best-known, non-strictly-surgical operations, which nevertheless generates stress for the dental arch and the underlying bone structure, is the removal of a tooth crown. As a matter of fact, a significant effort is required to detach the artificial crown from the tooth stump or from the implant pin anchored in the bone, breaking the bond of general glues or cements without damaging the stump or implant pin from the bone. More invasive actions are the ones relating to implant techniques—for example the insertion of implant pins into the lower jaw bone—which represent surgical procedures by now carried out routinely in dental surgeries. With reference to this last operation mode, in particular, over the last few years insertion procedures of the implant pin into the tooth socket are used, also in the proper body locations with insufficient bone volume and thickness. In order to be able to carry out these implantology procedures in a post-extraction tooth socket (see FIG. 1), however, it is necessary to act on the bone, to create the housing for the implant and possibly to perform an augmentation of the maxillary sinus, in a distal region of the jawbone (see FIGS. 2-4): the horizontal and vertical expansion of the jawbone is traditionally performed by using osteotomes in association with a manual surgical hammer. In particular, the operation may be of three different types:

a. horizontal expansion of the bone ridge of the upper jawbone, b. vertical expansion of the jawbone, with deformation and shifting of the jawbone floor and sinus, c. horizontal and vertical expansion of the jawbone (with creation of a vertical slot, in the mesio-distal direction within the mouth-palate thickness of the residual bone ridge, and two releasing intra-bone incisions, a mesial one and a distal one).

However, also in the orthopedic field surgical techniques exist which require the application of percussive actions. For example, the extraction of temporary screws or nails from bone masses requires a hammer percussion action; such operations are often made difficult by the calcification of the screws or of the nails in the bone.

Moreover, for the insertion of prosthesis or connection means into bones, the technique of obtaining also the implant seats, instead of through the use of rotary mills causing wear of bone mass and in biologically unsuitable in-situ overheating, through osteotomes beaten by the manual surgical hammer has become established. Through such technique, sliding and bone compacting is obtained, beat upon beat, which enables the physician to assess each time the result obtained.

In all these cases of bone surgery, the forces/accelerations which can be imparted manually, through a surgical hammer, have a modulus and direction which cannot be predetermined precisely, neither can they be constant, nor repeatable. The operator hence performs continuous adjustments which make the operation longer and more painful than necessary. Moreover, the forces applied manually last relatively long (in the order of tenths of a second) so that, given their physical nature, they deform the spongy part of the bone in an extremely limited manner; this occurs since the majority of the force is expressed accelerating the entire affected bone structure, for example the cranial-facial one. Consequently, in addition to not producing an effective action localised on the bone, the inertial impacts which reflect on the entire bone structure of the skull may determine influences on the internal part of the patient's ear and painful conditions; as a matter of fact, the patient's head undergoes a significant acceleration, while the otoliths tend to maintain their state due to inertia: an acceleration of the otoliths with respect to the maculae results; in the cases in which the acceleration exceeds the force of adhesion to the cilia, a detachment of the otoliths occurs, due to the large mass thereof compared to the initial speed of the system. This causes vertigo to the patient (Benign Paroxysmal Positional Vertigo, or cupulolithiasis) the main symptom of which is balance distortion, caused by the detachment of the otoliths.

These practices have shown that it is very difficult for the surgeon to be able to maintain the alignments and obtain the correct compacting thickness of the spongy mass of the bone.

Another critical aspect of the manual practice is the execution of the "split crest" technique: the manually caused impact hardly aids the dilation of the bone ridge and easily causes complications, among which the break of the bone ridge, with resulting problems in the positioning of the implant pin.

This comes in addition to the problem concerning the accessibility to the innermost part of the jawbone and of the upper jaw, seat of the molar teeth.

The prior art already offers some electrical devices suited to create more repeatable mechanical actions, which replace the forces which can be manually exercised by the surgeon.

Typically, instruments provided with a longitudinally movable cursor (or mass) through the action of linear motors or of suited configurations with magnetic coil have already been offered.

However, so far these instruments have not proved fully satisfactory for various reasons. They are generally conceived to perform an alternate, vibrational motion of a work tool, which hence substantially allows to perform a cutting/sawing action and in any case with an erosive function with resulting bone mass wear, with minimal forces and with alternate, continuous movement. Since these instruments are not designed to absorb and develop large amounts of energy, they fully differ from the need referred to in the present treatment. The continuity of the alternate action prevents from delivering large amounts of energy. Therefore the short continuous and alternate movements of these devices, even though they do not create the bad clinical conditions listed above, are unable to act as desired on the local bone structure or to effectively detach calcified bridges, crowns or screws.

GB 316,478, for example, describes a tool-actuating device, which includes a moving slider acting like a hammer. The tool is integral with the terminal part of a housing body. The slider is maintained in a home position by a compression spring and is guided in a tubular element: it is accelerated directly against the tool through a solenoid reel. A vulcanised rubber element is furthermore provided between the slider and the tool, to avoid magnetic sticking: this greatly dampens the impulsive action of the slider on the tool. Moreover, the low working voltage (a 6V or 24V battery) and the presence of a complex mechanism for supplying on/off electric power with a certain frequency cause the device to work with little energy and continuously with a certain frequency, supplying precisely that prolonged and alternate action which has been proved ineffective for the applications considered here.

U.S. Pat. No. 2,480,451 illustrates a device which provides again a low-energy, vibrating/oscillating movement of a tool, under the impulse of an alternated current. Such device is conceived to impart an alternate pressure of varying entity, but the force is minimal and prolonged in time, because it is sufficient, for example, to compact the filling in a tooth.

U.S. Pat. No. 6,171,312 concerns a controlled osteotome. In this case the tool is moved through cam system which are unable to impart any impulsive force, but rather a repetitive and low-modulus force. Through gears and crank gears it is not possible to express effective impulsive forces, because the inertial forces and the numerous couplings prevent from transferring translational momentums in a short time. As a drive system, the use of a cursor movable under the action of a solenoid operating alternately in an excited/disexcited mode is also generically suggested; no specific configuration nor solenoid operation mode is provided; on the basis of how the solenoid is shown, moreover, it does not even seem that it is able to impart a significant action: as a matter of fact, due to the shape of the magnetic field, the cursor is always attracted towards the solenoid centre and cannot protrude therefrom by a length greater than half the length thereof.

All these devices are designed to have a continuous and low-modulus movement, so as to perform mainly an erosive action. This result is the opposite to what has been obtained by the manual technique of the osteotomes beaten by the surgical hammer, which technique can be considered the most valid one to obtain bone mass compacting, but which carries the disadvantages set forth above.

The Applicant has realised that the energy transferred by these devices—through alternate, low-intensity forces, and prolonged over periods of time—is not adequate for obtaining an effective result in this specific sector.

Through in-depth studies and subsequent comparison tests, the Applicant has considered it more effective to fully shift the problem approach, by supplying a tool which, despite using overall power levels equivalent to the known ones (to be able to resort to conventional electric network supplies available in medical surgeries), distributes the energy in a definitely different and original manner, which is more effective for this specific application.

SUMMARY OF THE INVENTION

The object of the present invention is hence to solve the drawbacks of the manual practices and of the prior-art devices, by offering a device which enables to achieve an effective action in the dental field and in the field of general bone surgery, so as to determine forces suited to bone implant surgeries and extraction of bridges or crowns, removal of nails or decalcification of screws from bone masses without drawbacks on the patient's health and easing the surgeon's task.

Faced with such a task, the Applicant has acknowledged that in the surgery on the bone structure it is important to consider the plastic deformation typical of the material, i.e. that phenomenon which leads a material to change shape over time, with different features depending on the load amount and on the time distribution thereof. The jawbone and upper jaw deformation behaviour is the result of the influence given by intrinsically suited loads (forces) and is linked to the application times of these forces, so as to ease the molecular creep or to make it more difficult. In particular, the times with which these forces are applied become essential for obtaining the desired deformation, without influencing with unwanted accelerations the centre of gravity of the mass on which the plastic deformations are performed.

The device according to the invention has hence been configured, neglecting the object of continuous operation, so as to produce a single, high-intensity impulse action which propagates in the tool (osteotome or crown-removing hook or screw remover) through a limited-duration impact, with a sound component followed by a translational momentum.

According to a first aspect of the invention, in particular, a percussion device for bone implants, nail removal, decalcification of bone joint screws or bridge or crown removal is supplied, comprising a housing body within which an electromagnetic coil is installed for the acceleration of a percussion anchor, the coil working to magnetise and demagnetise the anchor and the yoke so as to control in one direction and in the opposite one the anchor, from the housing body a metal tool stem furthermore projecting, further comprising a sonic rod which crosses the core of said electromagnetic coil and along which said percussion anchor slides, said sonic rod comprising a terminal head with which said metal tool stem can be integrally coupled, at least in a longitudinal direction, a floating yoke arranged in the proximity of said terminal head which acts as travel end stop for said anchor, and wherein said electromagnetic coil is overcharged impulsewise with a current having a duration below 20 milliseconds and an energy ranging between 800 and 1200 W, so as to control in a first direction said anchor and produce an impact of said anchor on said yoke, closing the electromagnetic flow, which develops an energy transfer to said tool stem through a sound wave and a subsequent translational momentum, the developed force ranging between 60 and 260 daN and such impulse energy being distributed for at least 80% in a time interval, in its maximum peak, not above 50 µs, preferably below 30 µs.

According to another peculiar aspect of the invention, an actuation method is provided of a percussion device for bone implants, or nail removal and screw decalcification from bone masses, of the type comprising a movable mass accelerated through an electromagnetic coil against a floating yoke suited to transfer the impact to a stem of a metal tool, wherein said electromagnetic coil is overcharged impulsewise with a current having a duration below 20 milliseconds and an energy level ranging between 800 and 1200 W, so as to produce an impact of said movable mass on said yoke which develops an energy transferred to said tool stem through a sound wave and a translational momentum, the developed force ranging between 60 and 260 daN and such impulsive energy being distributed for at least 80% in a time interval, in its highest peak, not exceeding 50 µs, preferably below 30 µs.

BRIEF DESCRIPTION OF THE DRAWINGS

Further features and advantages of the device according to the invention will in any case be more evident from the following detailed description of some preferred embodiments, given by way of example and illustrated in the attached drawings, wherein.

DETAILED DESCRIPTION OF SOME PREFERRED EMBODIMENTS

Figure 1:
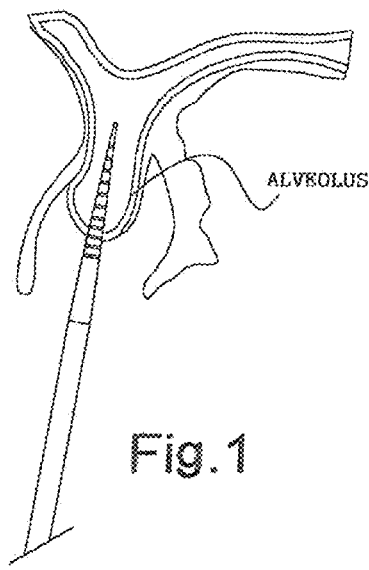
FIGS. 1-4 are schematic cross-sections of a jawbone showing the sequence of an exemplifying surgical operation through an osteotome.
Figure 2:
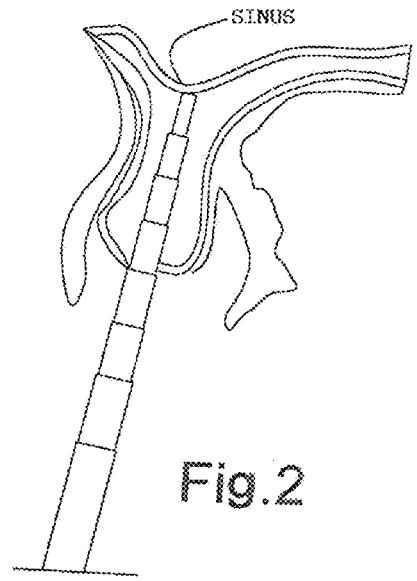
Figure 3:
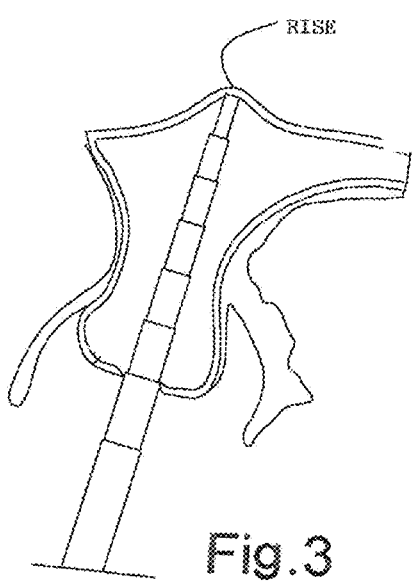
Figure 4:
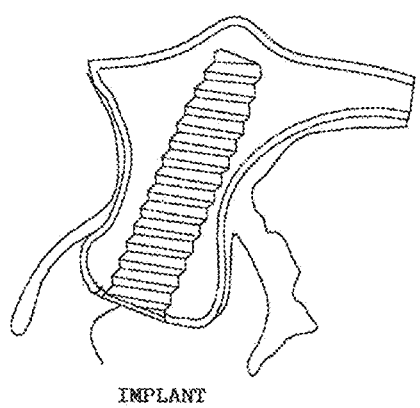
Figure 5:
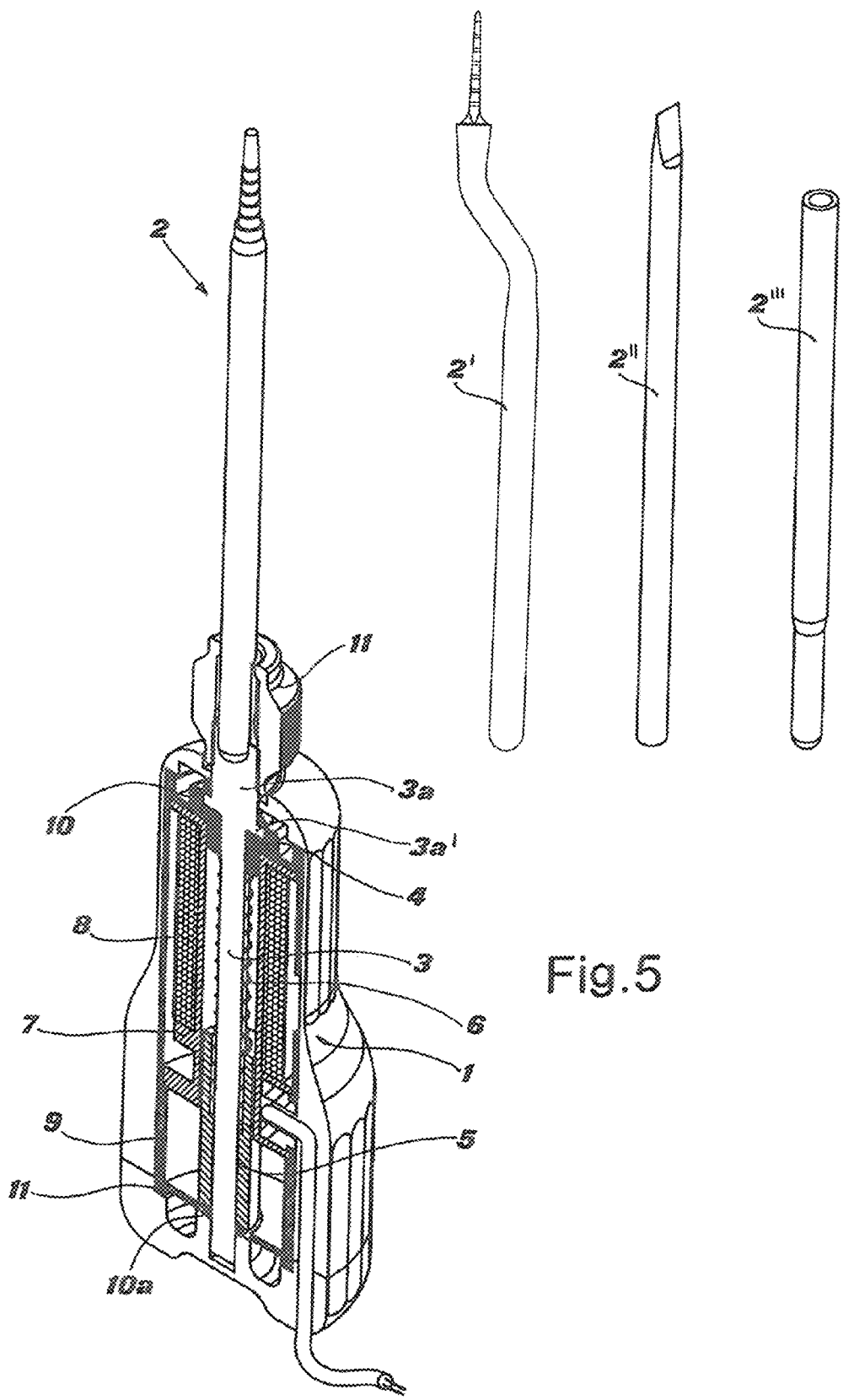
FIG. 5 is a perspective view, partly in section, of a device according to the invention in an osteotome configuration with relative possible tools.

With reference to FIG. 5, a first embodiment is illustrated of the device according to the invention, configured so as to act as bone compactor.

The device essentially comprises a containment housing 1, of such a shape and size as to be able to represent also the device handle, wherefrom an operating tool 2 projects, through which the desired force is transferred to the dental or bone tissue/member.

Housing 1 holds inside an electromagnetic coil or solenoid, supplied by an electric wire, in the core of which a sonic rod and an anchor 5 of ferromagnetic material slidingly mounted along the axis of rod 3 and preferably coaxial with said rod are contained.

At one end of the travel of anchor 5 an abutment yoke is provided, against which anchor 5 is intended to impact. The yoke is integral, at least in a longitudinal direction, with sonic rod 3 and is immersed in the magnetic field generated by the electromagnetic coil, so as to close the field flow.

The electromagnetic coil is caused to operate so as to magnetise and demagnetise the anchor and the yoke, so as to control impulsewise the anchor in a first direction towards the yoke and then in a second direction opposite thereto, to bring the anchor back into the home position thereof.

Anchor 5 is slidingly mounted along rod 3 and is preferably maintained at one home end of the travel thereof with the aid of a spring 6 or of another elastic means. Anchor 5 is in the shape of a small, hollow cylinder of a modest size and weight, for example 8-15 mm diameter, preferably 10 mm, 20-40 mm long, preferably 30 to 35 mm, and with a mass of about 6-17 gr, preferably 10 gr. Moreover, in order to be able to develop sufficient kinetic energy (the size and delivered energy being the same), it is suitable for the free travel of anchor 5, between the home position and the impact travel end position (as will be better described in the following) thereof to be in the order of 30-50 mm.

It must be considered that, in order to obtain a useful translational momentum, it is nevertheless possible, within the intervals supplied, to change accordingly the anchor mass and the travel thereof; for example, the same result in terms of translational momentum can be obtained by reducing the mass and increasing the travel (increasing accordingly the length of the coil and of rod 3) or vice versa. Thereby the interval of obtainable forces becomes very wide.

In the embodiment illustrated in FIG. 5, the home position of anchor 5 is on the opposite side with respect to tool 2, i.e. towards the proximal end of handle 1. As a matter of fact, for the operation of the device acting as bone compacter, anchor 5 must be accelerated towards the free end of tool 2, hence upwards in the representation of FIG. 5.

The electromagnetic coil comprises a bobbin 7, whereon a solenoid 8 is wound, and it is enclosed by a skirt 9.

Rod 3 is mounted substantially movable in an axial direction with respect to handle 1, by a short travel in the order of 1 mm with respect to housing 1 and to the electromagnetic coil and protrudes beyond the end of said coil. Rod 3 is retained, in the proximity of the ends thereof, on housing 1 preferably by arranging in between two O-rings 10 and 10A on the two opposite sides, outside the area occupied by the coil.

The distal end of rod 3 shows a head 3a which partly protrudes from the body of housing 1, through an exit port of housing 1. At the bottom of head 3a there is provided a flanged portion 3a', arranged inside housing 1: on the outermost side of the flanged portion 3a' there is installed O-ring 10, which acts as buffer and spacer with respect to the wall of housing 1, while on the innermost side there is arranged floating yoke 4 axially constrained to sonic rod 3 and floating therewith. The head portion 3a which protrudes outside housing 1 is configured so as to be able to define a coupling seat with tool 2, in particular a steel osteotome or "bone expander", complying with the relevant regulations. Tool 2 may take up various shapes (referred to by numbers 2', 2" and 2''') depending on the surgical operations to be performed.

A possible coupling mode is illustrated in FIG. 5: the outer portion of head 3a has a threaded outer surface suited to engage with a corresponding inner threading of a mandrel or tightening bush 11. The tool can be simply placed abutting from head 3a—creating an intimate contact and material continuity between the tool and head 3a—introducing the bottom end of tool 2 into a hollow seat of head 3a and locking tool 2 at head 3a by tightening mandrel 11. Once the mandrel has been tightened, tool 2 and sonic rod 3, through head 3a, are perfectly consolidated in an axial direction.

For a correct operation of the device, the longitudinal axis of elongated tool 2 must be coaxial with the longitudinal axis of sonic rod 3.

Floating yoke 4 can be obtained as a separate element, made of ferromagnetic or non-magnetic material (for example with a mass of 5 gr, 12 mm diameter and 5.5 mm height) or it can be obtained integrally with sonic rod 3. Yoke 4 is floating in the sense that it is fastened and integral with sonic rod 3, itself being movable in an axial direction with respect to the device housing with a travel in the order of 1 mm, in order to be able to exploit both the sonic waves and the translational momentum.

The object of yoke 4 can be twofold. On the one hand, if it is built of ferromagnetic material, it allows to close the magnetic flow of the electromagnetic coil, to the closure of which anchor 5 also participates, so as to create a magnetic field capable of effectively accelerating the anchor or movable mass 5 as far as the end of the travel thereof. On the other hand, it represents a travel end stop, against which movable anchor 5 impacts at the end of the travel thereof: in order to guarantee good duration thereof, or a different behaviour in the impact transmission, it can be made of hardenable ferromagnetic material or of titanium.

Depending on the yoke composition, it has also been noticed that the nature of the impact impulse transmission differs. As a matter of fact, in case the yoke is made of ferromagnetic material, the closing of the magnetic field causes a contrast magnetic force to be generated at the time when the anchor impacts with the yoke, with a resulting reduction of the translational momentum transferred to the tool (in such case, the impulse component transmitted by the sonic wave takes up a greater percentage value than in the case of a non-ferromagnetic yoke).

In the case in which the yoke is built of hardenable, grade-5 titanium, hence non ferromagnetic, the impulse transmitted per translational momentum takes up a greater value in percentage than in the case of a ferromagnetic yoke.

By oversupplying the electromagnetic coil with adequate current (for example 0.8 to 1.2 KWatt in times in the order of 10 to 20 millisec), an impulsive magnetic field is generated which attracts ferromagnetic anchor 5 towards the coil core, shifting it from the home position thereof (illustrated in FIG. 5) in the direction of yoke 4. The force acting on anchor 5 produces a significant acceleration on the small mass thereof, which hence impacts with high energy and speed against floating yoke 4 integral with sonic rod 3.

As a matter of fact, the oversupply concept provides for the electric power delivered to the coil to be far higher than the design supply which the coil could tolerate (in terms of sizing and heating) with a continuous operation. The oversupply is hence made possible by the impulsive operation of the device, which provides an impact of mass 5 on yoke 4 and a discrete time interval (in the order of 1 sec or more) before the surgeon decides to impart the following one.

As a general rule, the acceleration with which said stress is transmitted must be in the order of tens of thousands of meters per square second, the application time of the impulse in the order of a few microseconds, while the forces at play can arrive at the level of the stresses which lead to the breakage of the materials which one wants to obtain the fracture or the plastic compacting of. The range of these parameters must in any case be modulated depending on the applications and the requirements which manifest therein.

The impact of anchor 5 on yoke 4, constrained to sonic rod 3, causes an energy transfer to the head 3a of the sonic rod and hence to tool 2, which occurs according to two modes: initially it is transferred through a sonic wave and subsequently also as translational momentum (short longitudinal displacement of the sonic rod and of the tool quantifiable in a travel below about 1 mm).

Sonic waves make up the intrinsic mechanical transmission system of the elastic perturbations and allow to transfer the impulsive energy from one section to the other of the stem of rod 3 (which acts as flow pipe). The energy exchange between the above-said sections occurs at the speed of sound (varying according to the material) which—in metals—is in the order of several thousands of meters per second. The limit of the transferable energy is represented by the ultimate tensile stress of the intended means, which for the selected materials is in the order of a thousand Newton per mm$^2$.

In substance (FIG. 6A) the invention device operates so as to produce an impulse stress I in a short time T1 and on the section A1 of sonic rod 3, so as to then have a good deal of the same energy in a time T2 on the terminal section A2S of tool 2, having the geometric shape necessary for punching or compacting.

In order to be able to obtain the impulse suited to cause the desired elastic wave on the tool tip, the best suited for the plastic deformation of the bone, a balanced choice has been made on the weights and sizes of the moving masses of the device.

The configuration of the invention, with the masses and energies selected as indicated as well as with the suited sizing of sonic rod 3 (which is longer than the coil length and at least equal to the travel of the mass of anchor 4), allows to work in the field of impulse stresses characterised by a very short application time and by high intensity. These are the ones by far best suited to effect the bone compacting operation or the loosening of the screws calcified in the bone or the crushing of the bonds of the adhesives in general or cements, without excessively stressing the bone mass (in particular the jawbone and hence the braincase) and, consequently, the acoustic apparatus as well as the patient's sensitivity. Therefrom it derives that mass, layout and geometry of the components which transmit the impact (moved by the electromagnetic flow) can be sized with various combinations with the fundamental aim of transferring the high impulse energy.

Figure 8:
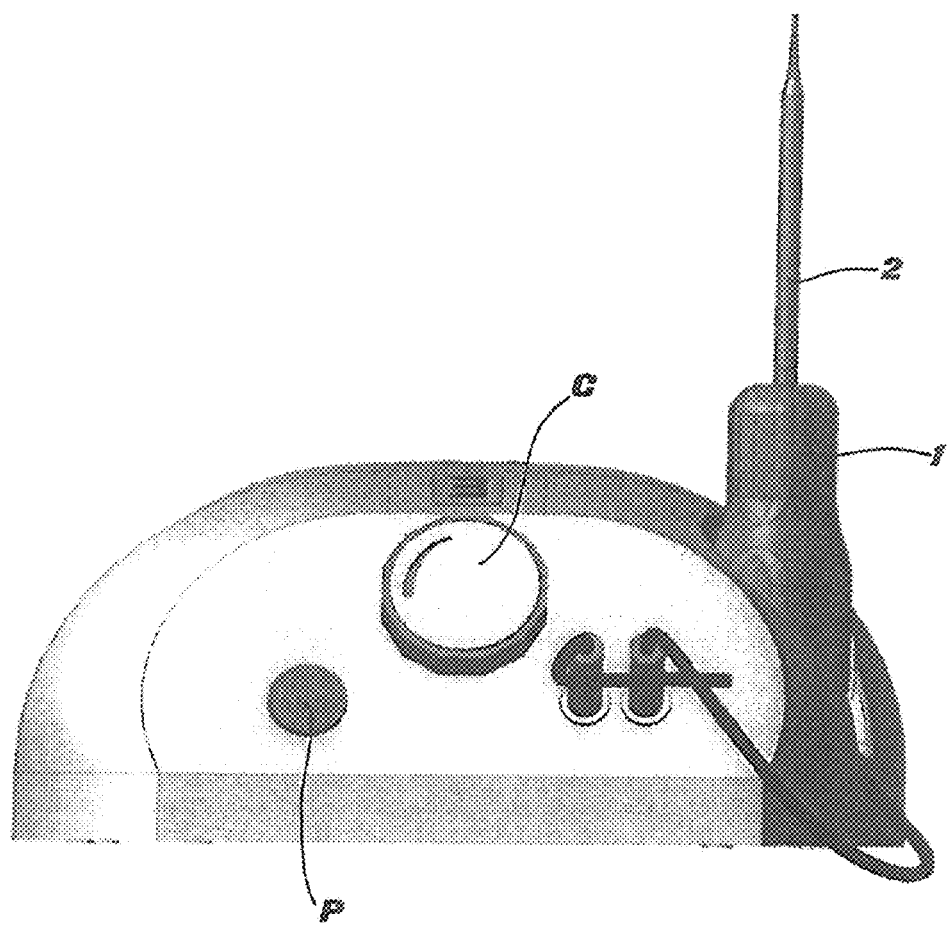
FIG. 8 is an elevation front pictorial view of an exemplifying embodiment of the complete apparatus according to the invention.

In use, the dental or bone surgeon applies to head 3a a tool 2 suited to the type of operation to perform, gripping then device housing 1. He then activates the device, acting for example on a switch button P (see FIG. 8 which exemplifies a possible configuration of the apparatus on the whole) so as to supply the electromagnetic coil with a value between 1 and 2.5 Ohm (preferably 1.8) with an impulse-type electric energy, possibly adjustable through a corresponding control knob C (for example a potentiometer). The coil is then energised for a very short time—for example between 1 and 40 milliseconds with a voltage between 12 and 60 volt—which allows to recall with a very high force moving anchor 5 into the reel, overcoming the action of spring 6. The anchor moves so quickly along the axis of stem 3 (first direction of movement) and impacts violently against floating yoke 4, closing the magnetic flow.

The impact—of short duration and high intensity—gives rise to a sonic wave which propagates along the terminal part of rod 3 and the stem of tool 2, followed by a transfer of the translational momentum of the abruptly decelerated anchor.

The initial sonic wave produces an elastic elongation of the theoretic stream pipe (rod 3), proportional to the type of material of which it is made. As already mentioned, for such purpose sonic rod 3 must have a discrete length, otherwise no significant effect would be exhibited. Rod 3 extends longitudinally within the entire solenoid and protrudes at the ends, on one side enough to define the flange coupling with abutment yoke 4 and on the other side to guide and support the anchor outside the solenoid in a home position. In substance, rod 3 has a length at least equal to the sum of the length of anchor 5 and of the travel thereof, i.e. exceeding an interval of 50-90 mm.

Through the sizing indicated above it is possible to produce a peak force at the tip of the metal tool lasting in the order of tens of microseconds, containing 80% of the energy of the impulse signal in a time window in the order of 50 to 30 μs with a maximum force ranging between 60 and 260 daN.

Figure 6:
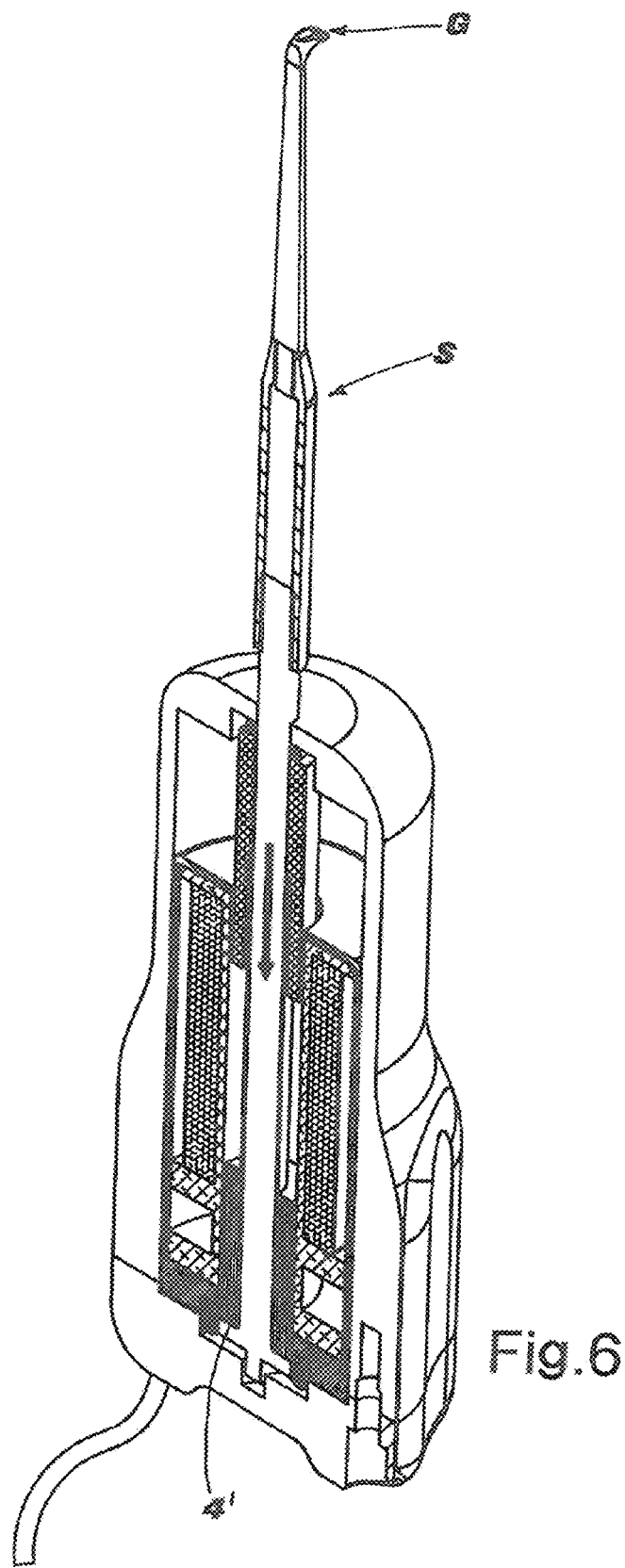
FIG. 6 is a perspective view, partly in section, of a device according to the invention in a crown-removing configuration.
Figure 6A:
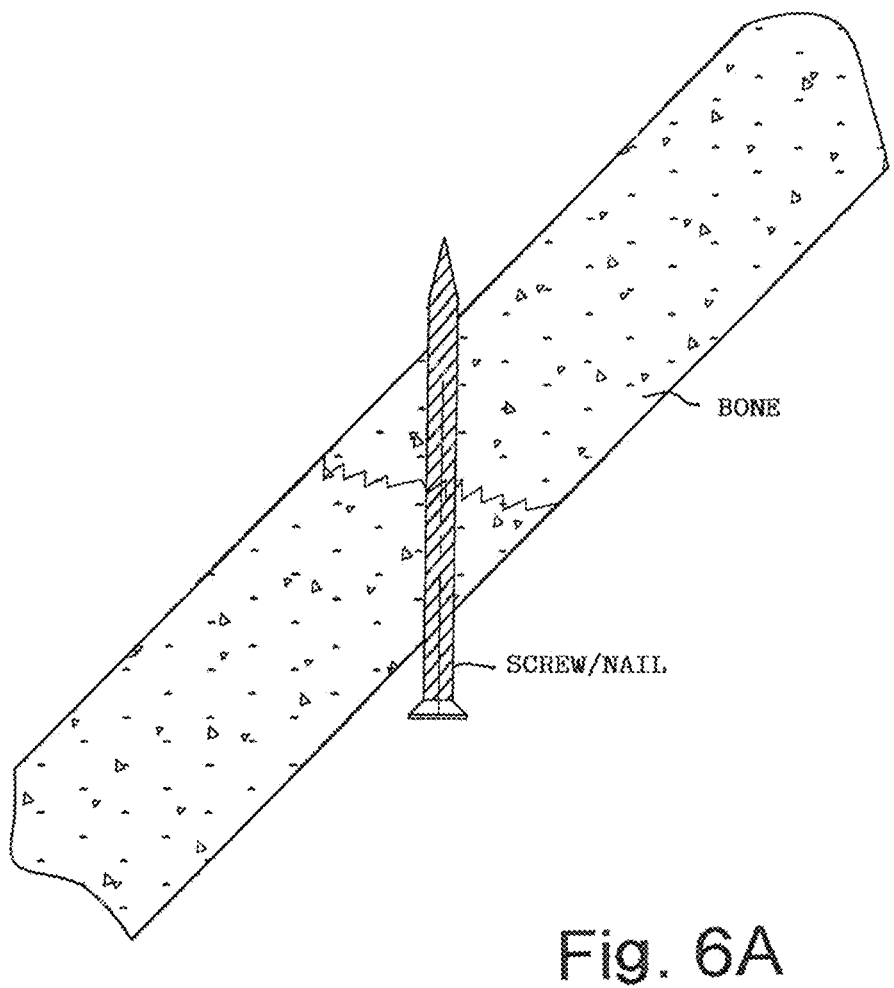
FIG. 6A is a schematic section view showing a possible application of the device according to invention.

Following the magnetisation which accelerates the anchor in the first direction, a demagnetisation obtained again through the coil brings the anchor back to the home position thereof. It is not provided to cause the device to operate in an alternate manner, since it would produce quick overheating (the electric power supplied is an overcharge, adequate to obtain the desired impulse energy despite limiting the device size, but that would make intolerable a continuous operation) and ultimately an incontrollable action. After a first energy impulse, the surgeon must assess the effect thereof and then he/she can possibly apply another one and so on. With reference to FIG. 6 of the drawings, the invention device takes up the appearance of an apparatus for the removal of crown or bridges, hence suited to brake a means of adhesion (usually an adhesive or cement) arranged between crown or bridge and tooth stump implanted in the bone structure.

Figure 7A:
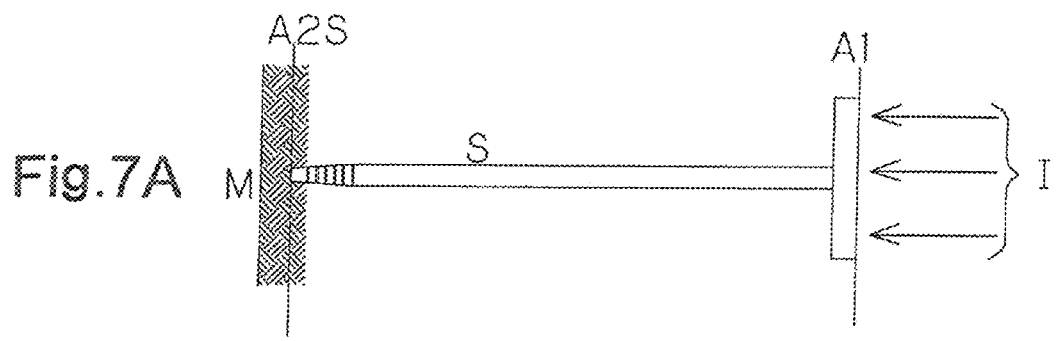
FIGS. 7A and 7B are schematic views which illustrate the operation principle of the invention.
Figure 7B:
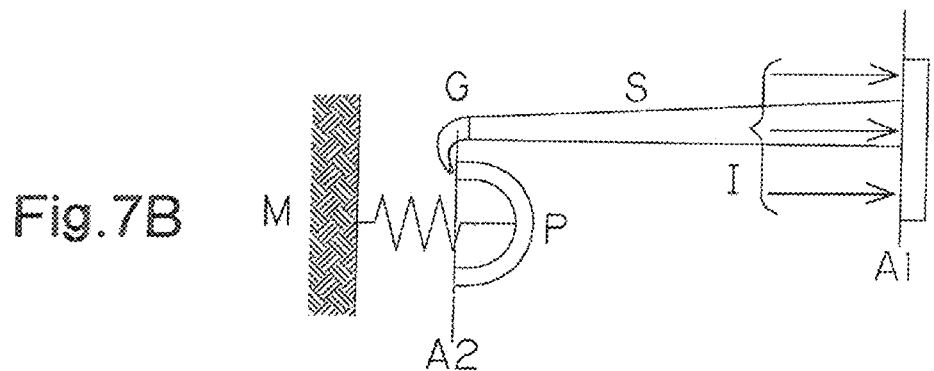

In this case, the operation tool is shaped as a tapered stem S, provided at the end thereof with removal means, such as a hook G, intended to impart the desired impulse action on the crown or the bridge (see also FIG. 7B).

For the rest, the crown-removing device is substantially identical to the one illustrated with reference to FIG. 5, except for the fact that the moving mass is intended to perform a reverse movement in determining the impulse action. In particular, the movable anchor has a home position in the proximity of the distal end of housing 1 and is accelerated towards the proximal end of the handle, i.e. moving it away from the tool. Also floating yoke 4' is hence arranged on the opposite side with respect to the first embodiment described above.

In this application, floating yoke 4' can be advantageously made of ferromagnetic material, since the detachment function of the tooth crowns is performed mainly through the effect of the sonic wave component of the impulse force.

As can be well understood from the above-reported description, the percussion device according to the invention fully achieves the objects set forth in the premise. As a matter of fact, the device can be used with different types of tools in a number of bone implant applications, particularly dental ones, both in order to deform and compact the bone structure, and to detach elements/prosthesis glued with general adhesives or cements or to loosen up screws calcified in bones.

By replacing the practice which used osteotome and manual surgical hammer, with accelerations far greater (in the range of microseconds) and in any case of predetermined, adjustable and repeatable force, one comes to the result that only the desired part of the bone mass gets plastically deformed; by deforming plastically, the affected mass is thus capable of locally absorbing the impact, thus avoiding to affect the rest of the patient's jawbone and inner ear. The result thus obtained hence allows to spare the patient any problem of vertigo and to obtain a radial performance devoid of fractures in the plastic reduction of the bone.

To such advantages the opportunity to guarantee greater precision for the surgeon must be added, who is assisted in the visibility during the operation, and greater mobility, since one hand only is engaged in bone compacting.

In substance the device overcomes known drawbacks by using a short-duration impulse force which transfers the energy to the bone structure through sonic waves and translational momentums with preconfigurable energy contents.

The energy transfer through sonic waves and very short displacements (translational momentums) of the tool opens the opportunity to use a new type of osteotome tool having a curvy shape (see FIG. 5 tool 2') which guarantees the operator accessibility to the innermost part of the jawbone (seat of the molar teeth) and to the entire lower jaw, thus enabling him/her to implement the practice of bone expansion also in such location.

Similarly, it is possible to employ a new housing tool (2''' in FIG. 5) which, due to the presence of a recess intended for the housing of an implant pin, enables the operator to insert the same into the intended bone cavity, using the sonic waves and impact waves which may be developed by the device. Thereby the pin insertion, before screwing thereof, is simplified.

Again, with reference to the application as crown-remover or extractor, with the device according to the invention it is possible to send elastic waves to the prosthetic structures causing an elastic deformation and the relative crumbling of the cement/adhesive or calcification, with the resulting detachment of the same but preventing the energy from propagating beyond and producing fractures of the stump tooth or from damaging the implant pin and from traumatising the radicolar-alveolar structure.

Figure 9:
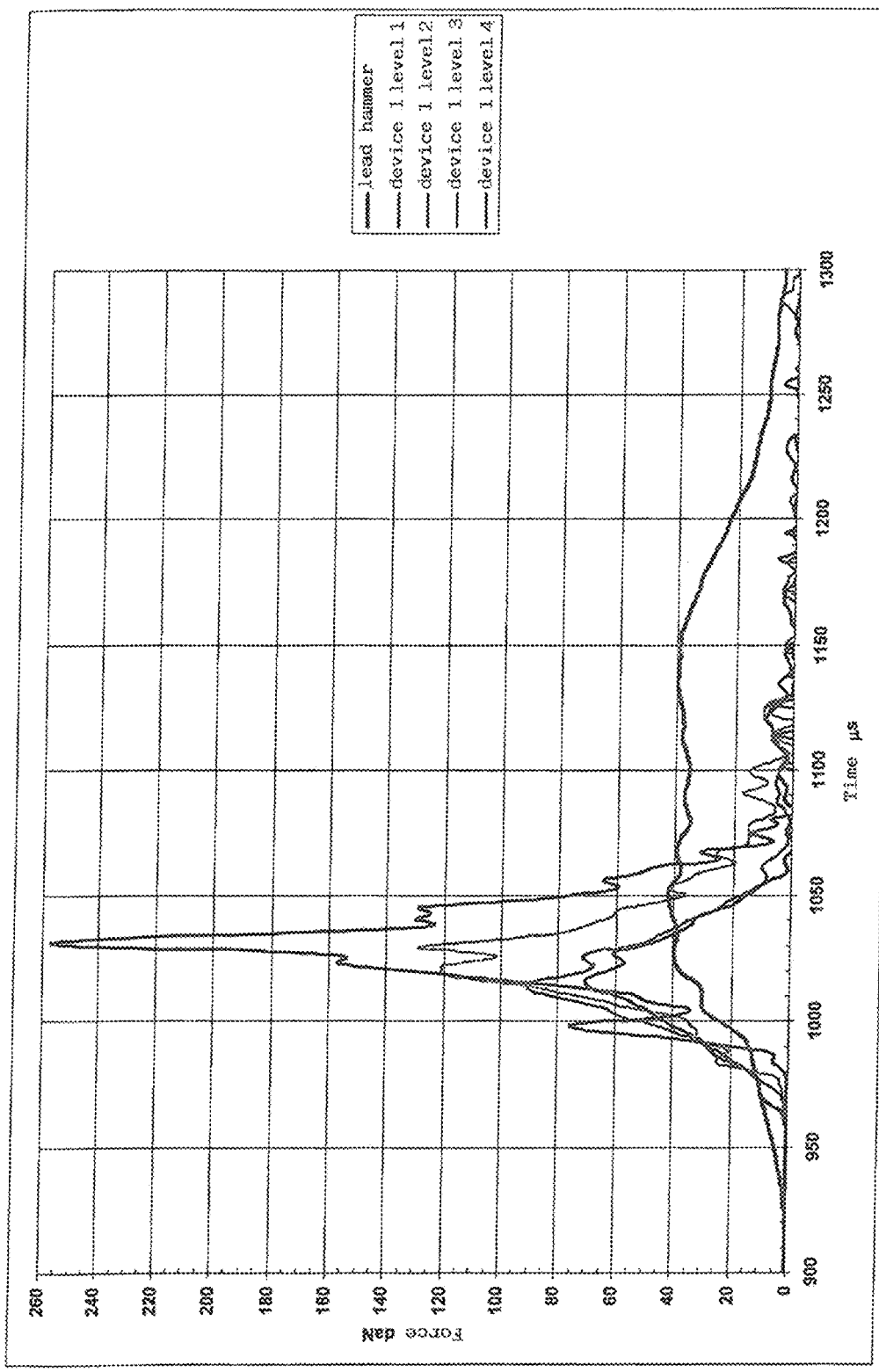
FIG. 9 is a diagram showing a comparison between the forces applied as a function of time.

It must be noted that, through a suitable adjuster C, the surgeon can in any case adjust the impulse force within the provided range (60-260 daN), so as to determine the action best suited to the desired operation. FIG. 9 shows various curves exemplifying the impulse signals for the different levels of force, also compared to a traditional impulse which can be obtained with a manual hammer. It is understood that other, different from the described ones, could be the embodiments of the procedure and of the device considered. Such embodiments and the variants thereof fall of course within the scope of the present invention as defined by the attached claims.

Finally, it is not ruled out that, instead of the return spring, the anchor can be guided back into its home position through a further auxiliary coil or a permanent magnet. The latter would have exclusively the function of withdrawing the anchor outside the main coil. For such purpose, the low-power, auxiliary coil may be housed in the device housing in correspondence of the home position of the anchor. In the active operation phase, such auxiliary coil could also be used to magnetise the anchor mass, so as to amplify the attraction effect into the main coil, which would help to impart impulse energy to the anchor.

The invention claimed is:

1. Percussion device for bone implantology or surgery extraction comprising a housing body (1) within which an electromagnetic coil is installed for the acceleration of a percussion anchor (5) and from which a stem of a metal tool (2) projects, characterised in that it comprises
    a sonic rod (3) which runs through the core of said electromagnetic coil and along which said percussion anchor (5) is slidable, said sonic rod (3) comprising a terminal head (3a) with which said stem of a metal tool (2) is integrally engageable, at least in a longitudinal direction,
    a floating yoke (4) arranged in the proximity of said terminal head (3a) which acts as travel end stop for said anchor (5), and wherein
    said electromagnetic coil is overcharged with a single impulse with a current of a duration shorter than 20 milliseconds and energy ranging between 0.8-1.2 KW, so as to accelerate in a first direction and produce an impact of said anchor (5) against said yoke (4) which develops an energy transferred to said tool stem (2) through a sonic wave propagating in said sonic wave and a translational momentum, the developed force ranging between 60 and 260 daN and such impulse energy distributing for at least 80% in a time range not above 50 µs.

2. Percussion device as claimed in claim 1, wherein said anchor (5) is mounted coaxially and slidable along said sonic rod (3) and is kept pushed at a home end of the travel thereof through elastic means (6).

3. Percussion device as claimed in claim 2, wherein said anchor (5) is shaped as a hollow cylinder having a diameter of 8-15 mm, a length of 20-40 mm and with a mass of about 6-17 gr.

4. Percussion device as claimed in claim 3, wherein the free travel of said anchor (5) is in the order of 30 to 50 mm.

5. Percussion device as claimed in claim 1, wherein said anchor (5) is accelerated by said coil towards the distal end of said tool (2).

6. Device as claimed in claim 2, wherein said sonic rod (3) has a length exceeding the sum of the length of said anchor (5) and of the travel thereof.

7. Percussion device as claimed in claim 2, wherein said anchor (5) is shaped as a hollow cylinder having a diameter of 10 mm, a length of 30 mm, and a mass of 10 gr.

8. Percussion device as claimed in claim 2, wherein said anchor (5) is shaped as a hollow cylinder having a diameter of 8-15 mm, and a length of 20-40 mm.

9. Percussion device as claimed in claim 2, wherein said anchor (5) is shaped as a hollow cylinder having a mass of 6-17 gr.

10. Device as claimed in claim 1, wherein said sonic rod (3) has a length exceeding the sum of the length of said anchor (5) and of the travel thereof.

11. Percussion device as claimed in claim 1, wherein said sonic rod (3) is mounted substantially movable in an axial direction, integrally with said floating yoke (4), with respect to said housing body (1), of a short travel in the order of 1 mm.

12. Percussion device as claimed in claim 11, wherein said sonic rod (3) is held on said housing body (1), in the proximity of the ends thereof, through the fitting of O-rings (10, 10A) arranged outside the area occupied by said coil.

13. Percussion device as claimed in claim 1, wherein a distal end of said sonic rod (3) has a head (3*a*) which at least partly protrudes from said housing body (1) and is configured as a seat of coupling with said tool (2).

14. Percussion device as claimed in claim 13, wherein a basic portion of said tool (2) is in intimate contact with said head (3*a*) and they are made integral in an axial direction.

15. Percussion device as claimed in claim 1, wherein said floating yoke (4) is made of ferromagnetic material.

16. Percussion device as claimed in claim 1, wherein said floating yoke (4) is made of titanium.

17. Device as claimed in claim 1, wherein the developed force ranges between 60 and 260 daN and the impulse energy distributing for at least 80% in a time range not above 30 μs.

* * * * *